US012272441B2

(12) United States Patent
Teixeira et al.

(10) Patent No.: US 12,272,441 B2
(45) Date of Patent: Apr. 8, 2025

(54) METHOD AND SYSTEMS FOR PREDICTING A STREAM OF VIRTUAL TOPOGRAMS

(71) Applicant: Siemens Healthineers AG, Forchheim (DE)

(72) Inventors: Brian Teixeira, Princeton, NJ (US);
Vivek Singh, Princeton, NJ (US);
Ankur Kapoor, Plainsboro, NJ (US);
Yao-jen Chang, Princeton, NJ (US);
Birgi Tamersoy, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 736 days.

(21) Appl. No.: 17/489,838

(22) Filed: Sep. 30, 2021

(65) Prior Publication Data

US 2022/0130524 A1 Apr. 28, 2022

(30) Foreign Application Priority Data

Oct. 27, 2020 (DE) .................... 10 2020 213 489.8

(51) Int. Cl.
*G16H 30/40* (2018.01)
*G06F 18/214* (2023.01)
*G06N 20/00* (2019.01)

(52) U.S. Cl.
CPC ......... *G16H 30/40* (2018.01); *G06F 18/2148* (2023.01); *G06N 20/00* (2019.01);
(Continued)

(58) Field of Classification Search
CPC .......... G06N 20/00; G06N 3/084; G06N 3/04; G06N 3/045; G16H 30/20; G16H 30/40;
(Continued)

(56) References Cited

U.S. PATENT DOCUMENTS

| 2010/0198101 A1 | 8/2010 | Song et al. |
| 2013/0245461 A1 | 9/2013 | Maier-hein et al. |

(Continued)

FOREIGN PATENT DOCUMENTS

| CN | 108990412 A | 12/2018 |
| CN | 109410273 A | 3/2019 |

(Continued)

OTHER PUBLICATIONS

Booij, Ronald, et al. Accuracy of automated patient positioning in CT using a 3D camera for body contour detection. European radiology, 2019, 29. Jg., Nr. 4, S. 2079-2088.
(Continued)

*Primary Examiner* — Ajibola A Akinyemi

(57) ABSTRACT

A stream of virtual topograms, in particular live virtual topograms, is predicted. Sets of surface data of an outer surface of a subject are continuously received. Based on each received set of surface data a (live) virtual topogram is continuously generated by a trained machine learning algorithm (MLA). Thereto, a representation of body landmarks is updated based on each received set of surface data by a trained body marker detector (BMD), of the trained MLA, and the (live) virtual topogram is predicted based on the updated spatial marker map and on the corresponding set of surface data by a trained topogram generator (TG) of the trained MLA.

19 Claims, 4 Drawing Sheets

(52) U.S. Cl.
CPC ............. *G06T 2207/10012* (2013.01); *G06T 2207/10081* (2013.01); *G06T 2207/30004* (2013.01)

(58) Field of Classification Search
CPC ........ G16H 40/63; G16H 50/20; G16H 50/50; G16H 50/70
USPC ........................................................ 382/128
See application file for complete search history.

(56) References Cited

U.S. PATENT DOCUMENTS

| | | | |
|---|---|---|---|
| 2016/0195856 A1* | 7/2016 | Spero | H05B 47/155 700/90 |
| 2018/0014805 A1 | 1/2018 | Ertel et al. | |
| 2018/0228460 A1* | 8/2018 | Singh | G01R 33/5608 |
| 2019/0057515 A1 | 2/2019 | Teixeira et al. | |
| 2019/0057521 A1 | 2/2019 | Teixeira et al. | |
| 2019/0164012 A1* | 5/2019 | Zisimopoulos | G06N 20/00 |
| 2019/0214135 A1 | 7/2019 | Wu | |
| 2020/0258243 A1 | 8/2020 | Chang et al. | |

FOREIGN PATENT DOCUMENTS

| | | |
|---|---|---|
| EP | 2441410 A1 | 8/2012 |
| EP | 3804624 A2 | 4/2021 |
| EP | 3865067 A1 | 8/2021 |

OTHER PUBLICATIONS

Eberhard, Matthias, and Hatem Alkadhi. "Machine learning and deep neural networks: applications in patient and scan preparation, contrast medium, and radiation dose optimization." Journal of thoracic imaging 35 (2020): S17-S20.

* cited by examiner

METHOD AND SYSTEMS FOR PREDICTING A STREAM OF VIRTUAL TOPOGRAMS

RELATED APPLICATION

This application claims the benefit of DE 10 2020 213 489.8, filed Oct. 27, 2020, which is hereby incorporated by reference in its entirety.

FIELD

The present embodiments relate to a computer-implemented method of predicting a stream of virtual topograms as well as a corresponding data processing system and a medical imaging system and, further, to a computer-implemented method of training machine learning algorithms (MLAs) for predicting virtual topograms as well as a corresponding data processing system.

BACKGROUND

Similar to real topograms or scouting scans obtained using medical imaging devices like computed tomography (CT) scanners, magnetic resonance imaging (MRI) devices, X-ray devices, sonography devices, and the like, a virtual topogram (synthetic topogram) provides a projected view of the internal anatomy (organs, etc.) of a patient. The virtual topogram is generated from depth information acquired with a (2.5D) depth sensor like a time-of-flight sensor, a light detection and ranging (LIDAR) sensor, a stereo camera, and the like by a trained machine learning algorithm (MLA), in particular a generative adversarial network (GAN). Thereto, the internal anatomy of a subject is estimated from the surface data, or, in other words, the virtual topogram, i.e., a two-dimensional (2D) projection of the internal anatomy of a subject, is predicted from geometric measurements on the subject's body surface. For example, a virtual topogram like a synthetic X-ray image of a subject is generated only from the surface geometry or depth information. The used architecture (trained MLA) may capture nonlinear correlation between the surface data and internal anatomy. The generated or predicted virtual topograms may serve as approximations of the true internal anatomy of subjects.

Current approaches to generate a virtual topogram only generate a one-shot (static) virtual topogram from one set of surface data. No temporal and movement information is considered and, consequently, no live or dynamic virtual topogram that depicts continuous movements such as breathing or movements of limbs can be generated.

Other approaches to represent the patient anatomy in real time are either with limited field of view (FoV) and poor resolution (sonography imaging) or time consuming (CineMRI).

SUMMARY

The object is to overcome or at least alleviate these problems by providing a computer-implemented method of predicting a stream of virtual topograms. A corresponding data processing system as well as a corresponding medical imaging system and, further, a computer-implemented method of training machine learning algorithms (MLAs) are provided for predicting a stream of virtual topograms.

According to a first aspect, a computer-implemented method of predicting a stream of virtual topograms, in particular live virtual topograms, includes the following acts:

Continuously receiving image data of a subject.

Continuously generating virtual topograms based on each received image data by a trained machine learning algorithm (MLA). The act of continuously generating virtual topograms includes the following acts:

Updating a representation of body landmarks, in particular internal body landmarks, based on each received image data by a trained body marker detector (BMD), of the trained MLA.

Predicting the virtual topogram based on the updated representation of body landmarks and on the corresponding image data by a trained topogram generator (TG) of the trained MLA.

According to a second aspect, a data processing system for predicting a stream of virtual topograms, in particular live virtual topograms, includes a processor or other device for carrying out the acts of the computer-implemented method according to the first aspect.

According to a third aspect, a medical imaging system for predicting a stream of virtual topograms, in particular live virtual topograms, includes an image acquiring device including an image sensor, the data processing system according to the second aspect, and an output device. The image sensor is configured to acquire image data of a subject. The data processing system is communicatively connected to the image acquiring device. The image acquiring device is further configured to continuously forward image data to the data processing system. The output device is communicatively connected to the data processing system. The output device is configured to receive the continuously generated stream of and/or live virtual topograms from the data processing system and to output the received stream of and/or live virtual topograms.

According to a fourth aspect, a computer program includes instructions which, when the program is executed by a computer, cause the computer to carry out the acts of the method according to the first aspect.

According to a fifth aspect, a computer-readable medium has stored thereon the computer program according to the fourth aspect.

According to a sixth aspect, a computer-implemented method of training machine learning algorithms (MLAs) for predicting virtual topograms, in particular live virtual topograms, includes the following acts:

Receiving a set of training data including training image data, corresponding training representations of body landmarks, and corresponding training topograms.

Providing an MLA configured to continuously receive sets of image data as input and to continuously generate virtual topograms from the continuously input sets of image data. The MLA includes a body marker detector (BMD), and a topogram generator (TG). The BMD includes trainable detector parameters. The BMD is configured to receive a set of image data as input. The BMD is further configured to update a representation of body landmarks based on the trainable detector parameters as output. The TG includes trainable generator parameters. The TG is configured to receive a representation of body landmarks and a set of image data as input. The TG is further configured to predict the virtual topogram based on the trainable generator parameters as output.

Training the MLA by:

Updating the trainable detector parameters based on a detector loss function penalising a difference between representations of body landmarks, which are generated from training sets of image data of the training data based on the trainable detector parameters, and the corresponding training representations of body landmarks of said training data.

Updating the trainable generator parameters based on a generator loss function penalising a difference between virtual topograms, which are generated from training sets of image data of said training data and corresponding representations of body landmarks based on the trainable generator parameters, and the corresponding training topograms of said training data.

According to a seventh aspect, a data processing system includes a computer for carrying out the acts of the computer-implemented method according to the sixth aspect.

According to an eighth aspect, a computer program includes instructions which, when the program is executed by a computer, cause the computer to carry out the acts of the method according to the sixth aspect.

According to a ninth aspect, a computer-readable medium has stored thereon the computer program according to the eighth aspect.

The present embodiments are particularly useful for non-invasive preliminary live imaging of subjects and for adjusting medical imaging devices (e.g., positioning of subjects in the device, adapting imaging protocols etc.).

The sets of image data include image data of an object, in particular of the subject or patient. The sets of image data can in particular be acquired or captured with the image sensor of the image acquiring device. In other words, the image sensor (e.g., CCD sensor, CMOS sensor, . . . ) captures the subject or patient. The sets of image data include image data of a two-dimensional (2D) image of the subject or patient. Thus, the subject or patient, or rather his position and orientation, is described by the image data of an 2D image of the subject or patient. The image acquiring device outputs the sensed 2D images. The image acquiring device may, therefore, in particular be a camera or video camera.

The image data may be position information of points of the subject or patient in a 2D Cartesian coordinate system recorded with the image sensor. Consequently, each set of image data may be a RGB image of the subject or patient.

The image sensor is directed at the subject or patient and may capture the subject or patient from one or more perspectives. Any portion of the subject or patient may be captured, such as the entire subject or patient from head to toe and hand to hand on one side or just the torso.

The term continuously, in particular, the term continuously receiving, generating, predicting, etc., is understood as in a "timely ordered manner" or rather in a "consecutive manner" possibly with gaps or omissions in between. Also said term is understood as meaning receiving a batch of timely ordered sets of data and processing one set of data after another or generating timely ordered sets of data and forwarding the latter as batch of timely ordered sets of data.

The image data are continuously received. In the context of the present embodiments, continuously receiving is understood as receiving one set of image data after another in a timely ordered way. For example, this can be accomplished via a live stream of image data that is received by the trained MLA. Correspondingly, the image acquiring device or rather the image sensor continuously acquires sets of image data of the object (e.g., subject, patient) and forwards the acquired sets of image data in a consecutive ore timely ordered way. However, the sets of image data can also be continuously received by receiving one set of image data after another of a stored batch of timely ordered sets of image data, or by receiving a batch of timely ordered sets of image data and processing one set of image data after another.

The (live) stream or batch of sets of image data includes information about the movement of the subject (e.g., movement of limbs, etc.) as the sets of image data is continuously acquired and forwarded to the MLA for generating the stream of virtual topograms, in particular the live virtual topograms. For example, information about the (continuous) movement of the limbs of the subject is included in the stream of sets of image data, as the changing location between the chest and the limbs of the subject is included in the pixels of each of the sets of image data or 2D images where the subject is depicted.

A virtual topogram, like a real topogram, depicts a region of a body of a subject or patient as two dimensional (2D) fluoroscopic or x-ray image or slice image or projection image. Consequently, the virtual or real topogram gives an overview over the internal state (e.g., internal organs, . . . ) of said region of the body. The real topogram can be generated via Magnetic Resonance Imaging (MRI), Computed Tomography (CT), x-ray imaging, ultrasound imaging or sonography, Positron Emission Tomography (PET), PET CT, and the like. Each generated or rather predicted virtual topogram resembles the type of real topogram (e.g., MRI, CT, x-ray, . . . ) based on which the MLA that generates or predicts the virtual topograms was trained. In other words, each virtual topogram has the same or at least similar image features (e.g., contrast, resolution, . . . ) as the corresponding real topograms used in training.

The virtual topograms, in particular the live virtual topograms, are continuously generated by the trained MLA from each received set of image data. Thus, a (live) stream of virtual topograms is generated by the trained MLA. Each generated or predicted (live) virtual topogram is a parametrized image and predicts the (current or live) internal anatomy of the subject even in movement. Each (live) virtual topogram is predicted from the respective received set of image data. Each (live) virtual topogram shows the atlas of the internal subject anatomy. Each (live) virtual topogram may be generated by the trained MLA from only the respective received set of image data (i.e., 2D image or RGB image) or from said received set of image data and other data, such as a corresponding set of surface data, movement data, or patient prior parameters (e.g., height, weight, body mass index (BMI), . . . ).

MLAs are algorithms that improve a performance automatically through experience or training. They build a model based on sample data, known as training data or training samples, in order to make predictions or decisions without being explicitly programmed to do so. Machine Learning (ML) involves creating a model, which is trained on some training data and then can process input data to make predictions. An MLA may use an Artificial Neural Network (ANN or just Neural Network NN), a decision tree, a Support Vector Machine (SVM), a regression analysis, a Bayesian network, a genetic algorithm, and the like.

For example, ANNs are systems, in particular computing systems, inspired by biological neural networks that constitute animal brains. ANNs "learn" to perform tasks by considering (labelled) examples or training data, generally without being designed with any task-specific rules. During an initial learning or training phase, ANNs automatically generate identifying characteristics from the (labelled) training data. ANNs include a collection of connected nodes called artificial neurons, which loosely model the neurons in a biological brain. Each connection (synapses in the biological brain) can transmit a signal from one node to another. A node that receives a signal can process the signal and then signal to subsequent neurons connected to the node. In common ANN implementations, the signal at a connection between nodes is a real number (e.g., 0 . . . 1), and the output of each artificial neuron is computed by some non-linear function of the sum of its inputs (from other nodes). The connections between nodes are called "edges". The edges in ANNs may each have a weight that is adjusted during training of the ANNs. The weight increases or decreases the strength of the signal at the corresponding edge. Nodes may each have a threshold such that the signal is only sent if an aggregate signal exceeds that threshold. Typically, nodes are aggregated into layers. Different layers may perform different kinds of transformations on their inputs. Signals travel from a first layer or input layer to a last layer or output layer, possibly after traversing the layers multiple times.

In other words, an ANN is a network of basic elements, the so-called nodes or artificial neurons, which receive input. After receiving input, the nodes change their internal state (activation) according to that input, and produce output depending on the input and activation. The network forms by connecting the output of certain nodes to the input of other nodes forming a directed, weighted graph. The weights as well as the functions that compute the activation of each node can be modified during initial learning or training, which is governed by a learning rule or paradigm.

A node receiving an input from at least one predecessor neuron includes the following components: an activation, the node's state, depending on a discrete time parameter, optionally a threshold, which stays fixed unless changed by a learning or training function, an activation function (e.g., hyperbolic tangent function, sigmoid function, softmax function, rectifier function etc.) that computes the new activation at a given time and the net input, and an output function computing the output from the activation (often the output function is the identity function). An important characteristic of the activation function is that it provides a smooth transition as input values change, i.e., a small change in input produces a small change in output.

An input node has no predecessor but serves as input interface for the whole ANN. Similarly, an output node has no successor and thus serves as output interface of the whole ANN. An ANN consists of edges or connections, each edge transferring the output of a node (predecessor) to the input of another, succeeding node (successor). Additionally, to the assigned weight an edge may have a bias term added to a total weighted sum of inputs to serve as a threshold to shift the activation function. The propagation function computes the input to the succeeding node (successor) from the outputs of preceding nodes (predecessors) and may include the bias value.

The deep NN includes more than one layer, preferably more than four layers, more preferably more than seven layers and most preferably ten or more layers. Each layer may include several neurons or nodes. Preferably, each layer may contain ten or more, more preferably 50 or more and most preferably 100 or more neurons.

A core objective of an MLA, i.e., of a learner, is to generalize from its experience. Generalization in this context is the ability of an MLA to perform accurately on new, unseen examples/tasks, i.e., input data, after having experienced one or more learning data sets. The training examples of the training data sets come from some generally unknown probability distribution (considered representative of the space of occurrences) and the learner or MLA has to build a general model about this space that enables it to produce sufficiently accurate predictions in new cases. The types of machine learning algorithms differ in their approach, the type of data they input and output, and the type of task or problem that they are intended to solve.

In particular, a learning or rather training rule or paradigm may be an algorithm which modifies the parameters (e.g., weights, thresholds of variables, etc.) of a respective MLA, in order for a given input to the MLA to produce a favoured output. This training typically amounts to modifying the parameters (weights and thresholds of the variables) within the MLA. Given a specific task to solve and a class of functions, learning means using a set of observations to find the one (or one of the) function of the class of functions, which solves the task in some optimal sense. This entails defining a cost function such that for the optimal solution the cost is minimal and no other solution has a cost less than the cost of the optimal solution. The cost function is an important concept in learning, as it is a measure of how far away a particular solution is from an optimal solution to the problem to be solved. Learning algorithms search through the solution space to find a function that has the smallest possible cost. For applications where the solution is data dependent, the cost must necessarily be a function of the observations, otherwise the model would not relate to the data. It is frequently defined as a statistic to which only approximations can be made. It is possible to define an arbitrary cost function; however, a particular cost function may be used either because it has desirable properties (e.g., convexity) or because it arises naturally from a particular formulation of the problem.

An MLA like for example an ANN can be discriminatively trained with a standard backpropagation algorithm. Backpropagation is a method to calculate the gradient of a loss function (produces the cost associated with a given state) with respect to the parameters (e.g., weights) in the MLA or ANN. The parameter updates of backpropagation can be done via stochastic gradient descent. The choice of the cost function depends on factors such as the learning type (e.g., supervised, unsupervised, reinforcement etc.) and the activation function. Commonly, the activation function and cost function are the softmax function and cross entropy function, respectively.

In other words, training an MLA or ANN essentially means selecting one model from the set of allowed models (or, in a Bayesian framework, determining a distribution over the set of allowed models) that minimizes the cost. Commonly some form of gradient descent is deployed, using backpropagation to compute the actual gradients. This is done by simply taking the derivative of the cost function with respect to the network parameters and then changing those parameters in a gradient-related direction. Backpropagation training algorithms fall into three categories: steepest descent (with variable learning rate and momentum, resilient backpropagation), quasi-Newton (Broyden-Fletcher-Goldfarb-Shanno, one act secant), Levenberg-Marquardt and conjugate gradient (Fletcher-Reeves update, Polak-Ribiére update, Powell-Beale restart, scaled conjugate gradient).

Common training paradigms include, for example, supervised learning, unsupervised learning and reinforcement learning.

Supervised learning algorithms build a mathematical model of a set of data that contains both the inputs and the desired outputs (labels). The training data includes of a set of training examples. Each training example has one or more inputs and the desired output, also known as a supervisory signal. In the mathematical model, each training example is represented by an array or vector, sometimes called a feature vector, and the training data is represented by a matrix. Through iterative optimization of an objective function (L), supervised learning algorithms learn a function that can be used to predict the output associated with new inputs. An optimal function will allow the algorithm to correctly determine the output for inputs that were not a part of the training data. Supervised learning uses a set of example pairs and the aim is to find a function in the allowed class of functions that matches the examples. In other words, the mapping implied by the data is inferred; the cost function is related to the mismatch between the mapping of the model e.g., ANN and the data and it implicitly contains prior knowledge about the problem domain. The cost may be the mean-squared error, which tries to minimize the average squared error between the MLA's or ANN's output and a target value over all the example pairs. For example, minimizing this cost using gradient descent for the class of ANNs called multilayer perceptrons (MLP), produces the backpropagation algorithm for training MLAs or ANNs.

Unsupervised learning algorithms take a set of data that contains only inputs, and find structure in the data, like grouping or clustering of data points. The algorithms, therefore, learn from test data that has not been labeled, classified, or categorized. Instead of responding to feedback, unsupervised learning algorithms identify commonalities in the data and react based on the presence or absence of such commonalities in each new piece of data. In unsupervised learning, some data is given and the cost function to be minimized that can be any function of the data and the MLA's/ANN's output. The cost function is dependent on the task and any a priori assumptions (e.g., implicit properties or parameters of the model, observed variables etc.).

Reinforcement learning is an area of machine learning concerned with how software agents ought to take actions in an environment so as to maximize some notion of cumulative reward. In machine learning, the environment is typically represented as a Markov Decision Process (MDP). Reinforcement learning algorithms do not assume knowledge of an exact mathematical model of the MDP and are used when exact models are infeasible. For example, reinforcement learning algorithms are used in autonomous vehicles or in learning to play a game against a human opponent. As in reinforcement learning, data is usually not given; it is instead generated by an agent's interactions with the environment. At each point in time, the agent performs an action, and the environment generates an observation and an instantaneous cost according to some (usually unknown) dynamics. The aim is to discover a policy for selecting actions that minimizes some measure of a long-term cost, e.g., the expected cumulative cost. The environment's dynamics and the long-term cost for each policy are usually unknown but may also be estimated. The environment is commonly modelled as MDP with states and actions with the following probability distributions: the instantaneous cost distribution, the observation distribution and the transition, while a policy is defined as the conditional distribution over actions given the observations. Taken together, the two then define a Markov chain (MC). The aim is to discover the policy (i.e., the MC) that minimizes the cost.

The MLA according to the present embodiments is trained to continuously generate a (live) virtual topogram from each (one at a time) received set of image data and optionally corresponding further data (e.g., sets of surface data, movement data, patient prior parameters). Thereto, the MLA includes the BMD and the TG. The BMD and additionally or alternatively the TG may be a NN, in particular a deep NN.

The BMD may, in particular, be an internal body marker detector (IBMD). The BMD or rather the IBMD is trained to update the representation of body landmarks (markers) or internal body landmarks or markers, respectively, based on each (the current) received set of image data. The representation of (internal) body landmarks includes the (most probable) locations of at least two different (internal) body landmarks. The at least two different body landmarks are characteristic anatomic features like chin, nipples, shoulders, navel etc. and, in particular, internal anatomic features, like lung top, liver top, kidney centre, etc.

The representation (internal) body landmarks may be a spatial marker map (heat map), where depth information (distance of surface of the subject or patient to the image acquiring device) of the (internal) body land marks is included in each pixel of the respective (internal) body landmark in a 2.5D image, or a three dimensional (3D) Cartesian coordinate system, where the location of the (internal) body landmarks is given by three coordinates for each pixel or rather voxel of the (internal) body landmarks.

The TG is trained to output the (live) virtual topogram based on the updated representation of (internal) body landmarks and on the corresponding set of image data. To update or refine the (live) virtual topogram, the (internal) body landmarks may move in a constrained fashion. For example, the lung bottom cannot be below the kidneys since that's physically not a possible setup.

Thus, of the pair of networks of the trained MLA (i.e., the BMD and the TG), one (the BMD) is trained to predict the location of the body landmarks (i.e., update the representation of body landmarks) from the set of image data, and the other (the TG) is trained to predict the (live) virtual topogram from said set of image data and the updated representation of body landmarks. To facilitate convergent behaviour during test phase, both networks may be jointly learnt. A bijection between the updated representation of body landmarks and the predicted (live) virtual topogram is thereby explicitly learned.

The set of training data or training samples includes the training sets of image data, the corresponding training representations of (internal) body landmarks, and the corresponding training topograms. For each training set of image data, its corresponding training representation of body landmarks represents the ground truth for training the BMD or rather IBMD. Likewise, for each training set of image data its corresponding training topogram represents the ground truth for training the TG. The training topograms may be topograms acquired with a medical imaging device like a CT scanner, an MRI device, an X-ray device, an ultrasound or sonography device, etc. The corresponding training sets of image data and additionally or alternatively the corresponding training representations of (internal) body landmarks may be derived from imaging data generated during acquiring the respective training topograms. In other words, the training sets of image data and the representations of (internal) body landmarks may be derived (i.e., via projection and (manual) classification, respectively) from the imaging data of the training topograms.

The provided MLA includes the BMD, in particular the IBMD, and the TG as paired networks. The BMD or IBMD updates or generates the representation of (internal) body landmarks based on the information contained in the received or input (training) set of image data using its trainable detector parameters. The TG predicts or generates the (live) virtual topogram based on the same received or input (training) set of image data and based on either the corresponding training representation of (internal) body landmarks or the updated or generated representation of (internal) body landmarks from the BMD or IBMD using its trainable generator parameters.

During training of the MLA, the BMD or IBMD and TG are either separately trained or trained end-to-end or both.

Thereto, the trainable detector parameters of the BMD or IBMD are updated depending on the difference between the representation of (internal) body landmarks generated from an input training set of image data by the BMD or IBMD and the corresponding training representation of (internal) body landmarks. The detector loss function penalises said difference and updates based on the resulting penalty the trainable detector parameters.

For separate training, the trainable generator parameters of the TG are updated, independent of updating the trainable detector parameters of the BMD or IBMD, depending on the difference between the virtual topogram, which is generated from an input training set of image data and the corresponding training representation of (internal) body landmarks, and the corresponding training topogram. The generator loss function penalises said difference and updates based on the resulting penalty the trainable generator parameters. The detector parameters and the generator parameters are separately updated until a predefined training stop criterion is fulfilled (e.g., convergence, max. number of iterations, etc.).

For end-to-end training, the trainable generator parameters of the TG are updated, right after updating the trainable detector parameters of the BMD or IBMD, depending on the difference between the virtual topogram, which is generated from the same input training set of image data input to the BMD or IBMD and from the representation of (internal) body landmarks generated by the BMD or IBMD, and the corresponding training topogram. The generator loss function penalises said difference and updates based on the resulting penalty the trainable generator parameters. The detector parameters and the generator parameters are iteratively updated until a predefined training stop criterion is fulfilled (e.g., convergence, max. number of iterations, etc.).

The BMD or IBMD and TG may be first trained separately and then end-to-end.

In particular, features (parameters) of nodes of the BMD or IBMD and TG may be learned (updated) by using any building blocks. For example, auto-encoder (AE) or restricted Boltzmann machine (RBM) approaches may be used. AE transforms data linearly, and then applies a non-linear rectification, like a sigmoid function. The objective (loss) function of AE is the expected mean square error between the input training data (training topogram, training representation of body landmarks) and generated data (virtual topogram, representation of body landmarks) using the learned features (updated parameters). AE may be trained using stochastic gradient descent or other approaches to learn the features leading to the best generated data. The objective function of RBM is an energy function. Exact computation of the likelihood term associated with RBM is intractable. Therefore, an approximate algorithm, such as contrastive-divergence based on k-act Gibb sampling or other, is used to train the RBM to generate the respective data from the input based on the updated features. As training of AE or RBM is prone to over-fitting for high-dimensional input data, sparsity or denoising techniques (e.g., sparse denoising AE (SDAE)) may be employed to constrain the freedom of parameters and force learning of interesting structures within the data. Enforcing sparsity within hidden layers (i.e., only a small number of units in hidden layers are activated at one time) may also regularize the network. In other embodiments, at least one unit is a convolution with ReLU activation or is a batch normalization with a ReLU activation followed by a convolution layer (BN+LeakyRU+convolution). At least one element of the group including max pooling, upsampling, downsampling, and softmax layers and units may be used. Different units may be of the same or different type.

The virtual topograms (i.e., live stream of virtual topograms) continuously generated by the trained MLA are forwarded to the output device. The output device may be a monitor for displaying the continuously generated (live) virtual topograms, i.e., live stream of virtual topograms, to a user (e.g., a radiologist, etc.) or an interface to a medical imaging device (e.g., CT scanner, MRI device, X-ray device, etc.) e.g., for controlling the medical imaging device.

With the present embodiments, a (live) stream of virtual topograms can be generated from timely ordered sets of image data of the subject, which (live) virtual topograms may be updated in real time following the subject's movements (intended movements, such as arms moving, as well as automatic movements such as breathing and heart beating). The generated (live) stream of virtual topograms may be used for planning a medical imaging procedure for the subject (e.g., more precise positioning of the subject compared to just using body markers) or for individually adjusting imaging protocols of the medical imaging procedure. Furthermore, positioning suggested by the system using a physically consistent generated live stream of virtual topograms may be more readily used by users (e.g., radiologists, etc.) as opposed to just the body marker points. The (live) stream of virtual topograms may also be used for detection of anomalies, patient positioning, interventional procedures, completion of a full X-ray from a partial X-ray image, or other uses.

According to a refinement, the sets of image data include corresponding sets of surface data of an outer surface of the subject. In the act of updating, the representation of body landmarks is updated based on each received set of image data including the corresponding set of surface data by the trained BMD. In the act of predicting, the virtual topogram is predicted based on the updated representation of body landmarks and on the corresponding set of image data including the set of surface data by the trained TG.

According to a further refinement, the image acquiring device further includes a depth sensor configured to acquire sets of surface data and optionally movement data of the subject. The image acquiring device is configured to continuously forward the sets of image data including the corresponding acquired sets of surface data and optionally the movement data to the data processing system.

According to a further refinement, the training sets of image data include corresponding training sets of surface data. In the act of updating the trainable detector parameters, the representations of body landmarks are generated from the training sets of image data including the corresponding training sets of surface data. In the act of updating the trainable generator parameters, the virtual topograms are generated from the training sets of image data including the corresponding sets of surface data.

The sets of surface data include surface data of an object, in particular of the subject or patient. The sets of surface data may be captured with the depth sensor of the image acquiring device. In other words, the depth sensor captures the outer surface of the subject or patient, while its image sensor captures sets of image data of the subject or patient in parallel. Thus, each set of image data includes the data of a 2D image of the subject or patient and additionally the depth data for each pixel of the 2D image. Thus, the outer surface of the subject or patient is described by the surface data captured as depths or distance from the depth sensor to different locations on the subject or patient in combination with the location information of the 2D image of the subject or patient. The image acquiring device outputs the acquired sets of image data of the 2D images and the corresponding acquired sets of depth data. Alternatively, the depth sensor measurements are processed to determine the outer surface information, such as stereoscopically determining the outer surface from camera images from different angles with image processing.

The image acquiring device may, therefore, in particular be a 2.5-dimensional (2.5D) image acquiring device. The 2.5D device may acquire the 2D images (i.e., sets of image data), where each pixel of the 2D images includes a corresponding depth data (i.e., the corresponding set of surface data).

The surface or rather depth data may be distances from the image acquiring device or rather its depth sensor (e.g., a frontal surface of the image acquiring device or depth sensor) to the outer surface of the subject recorded with the depth sensor. The depth sensor may be a camera or cameras capturing a grid projected onto the subject via a (infrared) light source of the depth sensor. Multiple cameras (e.g., two cameras of a stereo camera) may reconstruct an outer surface from multiple images without transmission of structured light. Other optical or non-ionizing depth sensors may be used. Further, depth information can be reconstructed from multiple 2D images captured with one camera from multiple viewpoints or even from a single 2D image using machine learning.

The depth sensor is directed at the subject and may capture the outer surface of the subject from one or more perspectives. Any portion of the outer surface may be captured, such as the entire patient from head to toe and hand to hand on one side or just the torso. The outer surface may be the skin of the subject or clothing of the subject. The depth sensor may use a frequency that passes through clothing and detects skin surface.

The sets of surface data are continuously received together with the corresponding sets of image data. In the context of the present invention continuously receiving is understood as receiving one set of timely ordered surface data after another. For example, this can be accomplished via a live stream of surface data that is received together with the corresponding live stream of image data by the trained MLA. Correspondingly, the depth sensor continuously acquires sets of surface data of the object (e.g., subject or patient) and forwards these in consecutive or timely ordered sets of surface data. However, the sets of surface data can also be continuously received by receiving one set of surface data after another of a stored batch of timely ordered sets of surface data, or by receiving a batch of timely ordered sets of surface data and processing one set of surface data after another.

The (live) stream or batch of timely ordered sets of surface data includes information about the movement of the subject (e.g., breathing, heartbeat, etc.) as the surface data is continuously acquired and forwarded together with the corresponding sets of image data to the MLA for generating the stream of virtual topograms, in particular the live virtual topograms. For example, information about the (continuous) movement of the chest of the subject is included in the stream of sets of surface data, as the changing distance between the outer surface of the chest of the subject or patient and the depth sensor (e.g., its frontal surface) is included in the pixels of the region of each of the 2D images where the chest of the subject or patient is depicted.

The MLA is trained to continuously generate a (live) virtual topogram from each (one at a time) received set of image data including the corresponding set of surface data. Thereto, the MLA includes the BMD, in particular the IBMD, and the TG. The BMD/IBMD and additionally or alternatively the TG may be a NN, in particular a deep NN.

The BMD or IBMD, is trained to update the representation of (internal) body landmarks (markers) based on each (the current) received set of image data including the corresponding set of surface data.

The TG is trained to output the (live) virtual topogram based on the updated representation of (internal) body landmarks and on the corresponding set of image data including the corresponding set of surface data.

Thus, of the pair of networks of the trained MLA (i.e., the BMD or IBMD and the TG), one (the BMD or IBMD) is trained to predict the location of the (internal) body landmarks (i.e., update the representation of (internal) body landmarks) from the set of image data including the corresponding set of surface data, and the other (the TG) is trained to predict the (live) virtual topogram from said set of image data including the corresponding set of surface data and the updated representation of internal body landmarks. To facilitate convergent behaviour during test phase, both networks may be jointly learnt. A bijection between the updated representation of (internal) body landmarks and the predicted (live) virtual topogram is thereby explicitly learned.

The set of training data or training samples includes the training sets of image data including the corresponding sets of surface data, the corresponding training representation of (internal) body landmarks and the corresponding training topograms. For each training set of image data including the corresponding set of surface data, its corresponding training representation of (internal) body landmarks represents the ground truth for training the BMD or IBMD. Likewise, for each training set of image data including the corresponding set of surface data its corresponding training topogram represents the ground truth for training the TG.

The corresponding training sets of surface data may be derived from imaging data generated during acquiring the respective training topograms. In other words, the training sets of surface data may be derived (i.e., via projection) from the imaging data of the training topograms.

The provided MLA includes the BMD, in particular the IBMD, and the TG as paired networks. The BMD or IBMD updates or generates the representation of (internal) body landmarks based on the information contained in the received or input (training) set of image data including the corresponding set of surface data using its trainable detector parameters. The TG predicts or generates the (live) virtual topogram based on the same received or input (training) set of image data including the corresponding set of surface data and based on either the corresponding training representation of (internal) body landmarks or the updated or generated representation of (internal9 body landmarks from the BMD or IBMD using its trainable generator parameters.

Thus, training of the MLA is accomplished as described above, but with the training sets of image data including the corresponding sets of surface data.

With the present embodiments, a (live) stream of virtual topograms can be generated from sets of image data including corresponding sets of surface data of the subject or patient, which (live) virtual topograms may be updated in real time following the subject's movements (intended movements, such as arms moving, as well as automatic movements such as breathing and heart beating). The generated (live) stream of virtual topograms enables, in particular, precise depiction of movement of internal organs like the lung during breathing based on the additional (depth) information provided by the sets of surface data.

According to a refinement, the acts of updating and predicting are iteratively executed. The representation of body landmarks is updated based on each received set of image data and based on the predicted virtual topogram by the trained BMD.

According to a further refinement, the BMD of the provided MLA is configured to further receive a topogram as input. In the act of updating the trainable detector parameters, the representations of body landmarks are generated from training sets of image data of the training data and additionally from a corresponding topogram based on the trainable detector parameters.

For each received set of image data, the acts of updating and predicting are iteratively executed. Thereby, the spatial marker map is iteratively refined (updated) based on the iteratively predicted (live) virtual topogram, which in turn is refined based on each refined spatial marker map. The two networks are applied iteratively in a loop until convergence or until another predefined prediction stop criterion is fulfilled (e.g., max. number of iterations, etc.).

By using the predicted (live) virtual topogram from the TG in updating the representation of (internal) body landmarks by the BMD, in particular the IBMD, (i.e., stacked pipeline), the networks ensure that the (internal) body landmarks and virtual topogram are consistent. If a (internal) body landmark is updated, the rest of the (internal) body landmarks are appropriately updated (if needed) by cycling the resulting topogram through the BMD or IBMD and again predicting a (live) virtual topogram by the TG based on the output representation of (internal) body landmarks.

For updating the trainable detector parameters during training of the MLA, the representations of (internal) body landmarks are generated from training sets of image data of the training data and from the corresponding topogram based on the trainable detector parameters.

The corresponding topogram is either a (live) virtual topogram generated by the TG during updating the trainable generator parameters in end-to-end training or the training topogram corresponding to the input training set of image data in separate training.

By iteratively refining, the representation of (internal) body landmarks and the (live) virtual topogram anatomical correctness of the generated "final" (live) virtual topogram can be significantly increased.

According to a refinement, in the first iteration, the representation of internal body landmarks is updated based on each received set of image data and based on either a predefined standard topogram or a preliminary predicted virtual topogram by the trained BMD or IBMD.

In the first iteration in the act of generating, there is no (live) virtual topogram predicted by the TG present, which can be used as input to the BMD or IBMD besides the current received set of image data for updating the representation of (internal) body landmarks. Thus, either the predefined standard topogram, which may be permanently stored in a data storage of the data processing system, or the preliminary predicted virtual topogram is used as input for updating or rather generating the representation of (internal) body landmarks in the first iteration.

The predefined standard topogram may be a normalised topogram used as common basis in all first iterations.

The preliminary predicted virtual topogram may be separately generated in each first iteration (e.g., by the TG or a separate preliminary TG) based only on the current received set of image data. Alternatively, the preliminary predicted virtual topogram may be the (final) generated virtual topogram predicted by the TG from the previous received set of image data (of the previous clock or sampling cycle).

In end-to end training of the BMD, in particular the IBMD, and the TG of the MLA, the BMD or IBMD may receive the predefined standard topogram or the training topogram corresponding to the training set of image data as input in the first iteration and then the (live) virtual topograms predicted by the TG in the subsequent iterations.

By using either the predefined standard topogram or the preliminary predicted virtual topogram in the first iteration, the number of necessary iterations can be decreased, as the first iteration yields better results compared to a first iteration with noisy or dummy input (white noise or just zeros or ones as input for the BMD or IBMD instead of a topogram).

According to a refinement, the preliminary predicted virtual topogram is either generated only based on the first received set of image data by either the trained TG or a trained primary $TG_p$, or generated from a pre-stored phantom or a pre-stored topogram based on patient prior parameters.

Either, the preliminary predicted virtual topogram is preliminarily predicted solely based on the current received set of image data by the trained TG or by the (separate) trained primary TG (specifically trained to predict (preliminary) topograms solely from the received set of image data).

Alternatively, the preliminary predicted virtual topogram is preliminarily predicted by the non-learning method of providing the preliminary predicted virtual topogram by generating it from a pre-stored phantom or a pre-stored topogram based on patient prior parameters.

The pre-stored phantom may be a 3D representation of a body (part) of a subject or patient, which pre-stored phantom may have been generated by medical imaging like MRI, CT, etc.

The pre-stored topogram may be a 2D projection image of a body (part) of a subject or patient, which pre-stored topogram may have been generated by medical imaging like MRI, CT, etc.

The patient prior parameters are parameters of the subject or patient for which the (live) stream of virtual topograms should be generated. The patient prior parameters can include height, weight, BMI, sex, age, and the like.

Based on the patient prior parameters of the subject or patient the pre-stored phantom may be appropriately scaled and then the preliminary predicted virtual topogram may be derived from the scaled pre-stored phantom by projection (in the desired plane (e.g., frontal plane, axial plane, lateral plain)). Alternatively, the pre-stored topogram may be scaled based on the patient prior parameters into the preliminary predicted virtual topogram.

Thus, the preliminary predicted virtual topogram used as first input to the BMD or IBMD in the first iteration can be predicted particularly efficiently.

According to a refinement, the method further includes the following act:

Continuously receiving movement data of the subject.

The representation of body landmarks is updated further based on the received movement data by the trained BMD.

According to a further refinement, the medical imaging system further includes a movement sensor, in particular a respiratory sensor and additionally or alternatively a heart sensor. The movement sensor is communicatively connected to the data processing system and configured to continuously forward movement data, in particular, respiratory movement data and additionally or alternatively heartbeat movement data of the subject, to the data processing system.

According to a further refinement, the set of training data further includes training movement data, in particular training respiratory movement data and additionally or alternatively training heartbeat movement data. The BMD is further configured to receive movement data, in particular respiratory movement data and additionally or alternatively heartbeat movement data as further input. In the act of updating the trainable detector parameters, the representations of body landmarks are generated further from training movement data, in particular training respiratory movement data and additionally or alternatively training heartbeat movement data.

The movement data may be or rather include body movement data, respiratory movement data, and additionally or alternatively heartbeat movement data. The movement data may be detected by the (separate) movement sensor or be derived by the depth sensor from the sets of depth data. Also, the depth sensor and the movement sensor may each provide movement data which are joined (e.g., mean value, weighted sum, etc.) into one set of movement data for generating the (live) virtual topogram. The (separate) movement sensor may for example detect body movement based on acceleration or change of position (acceleration or position sensor), respiratory movement based on movement of the chest (chest strap with strain gauge(s)), and heartbeat movement based on pulse or blood pressure measurement (ECG device, pulse monitor, blood pressure monitor, etc.). In particular, the (separate) movement sensor may be a fitbit, apple watch, pulse monitor, ECG device, and the like.

The movement data is provided to the BMD or IBMD as additional input and used besides the set of image data to update the representation of (internal) body landmarks. Thus, two sources of information regarding movement of the body or organs or rather the (internal) body landmarks of subject are utilised in updating the representations of (internal) body landmarks.

With the movement data as additional input (source of information) the representations of 8internal) body landmarks can be more precisely updated.

According to a refinement, the trained TG and additionally or alternatively the trained BMD is a generative adversarial network (GAN), in particular a Wasserstein GAN.

According to a further refinement, the TG and additionally or alternatively the BMD is a generative adversarial network, GAN, in particular a Wasserstein GAN. Updating the trainable generator parameters and detector parameters, respectively, includes comparing of the generated virtual topograms with the training topograms and the generated representations of body landmarks with the training spatial marker maps, respectively, by a topogram discriminator (TDC) and a map discriminator (MDC) respectively, and simultaneously updating trainable parameters of the TDC and of the MDC, respectively.

A generative adversarial network (GAN) is a class of machine learning algorithms (MLAs). Two neural networks (NN), namely a generative network (generator) and a discriminative network (discriminator), in particular a classification network, contest with each other in a game (in the sense of game theory, often but not always in the form of a zero-sum game) during training of the GAN. Given a training set, a GAN learns to generate new data with the same statistics as the training set. For example, a GAN trained on photographs can generate new photographs that look at least superficially authentic to human observers, having many realistic characteristics. GANs are commonly used in unsupervised learning, but can also be used in semi-supervised learning, (fully) supervised learning, and reinforcement learning.

In training of a GAN, its generator generates candidates while its discriminator evaluates them. The contest operates in terms of data distributions. Typically, the generator learns to map from a latent space to a data distribution of interest, while the discriminator distinguishes candidates produced by the generator from the true data distribution. The generator's training objective is to increase the error rate of the discriminator (i.e., by producing novel candidates that the discriminator classifies as part of the true data distribution).

A known dataset serves as the initial training data for the discriminator (classification network). Training the discriminator involves presenting it with samples from the training dataset, until it achieves acceptable accuracy.

The generator is trained based on whether it succeeds in generating candidates that the discriminator classifies as belonging to the true data distribution. Typically, the generator is seeded with randomized input that is sampled from a predefined latent space (e.g., a multivariate normal distribution). However, specific training input data can be provided to the generator instead of randomized input, e.g., image data for an image-to-image generator. Thereafter, candidates generated (synthesised, predicted) by the generator are evaluated (classified) by the discriminator.

Backpropagation is applied in both networks so that the generator produces better candidates (e.g., images), while the discriminator becomes more skilled at correctly classifying candidates generated by the generator as not belonging to the true data distribution.

The generator is typically a de-convolutional neural network, and the discriminator is a convolutional neural network. The GAN may include one or more convolutional neural networks (CNNs) as generator/discriminator, in particular an encoder and a decoder, which may have a U-net structure, with skip connections between them.

A U-net is a convolutional network architecture for fast and precise segmentation of images in particular of (bio) medical images. It is based on the fully convolutional network and its architecture was modified and extended to work with fewer training images and to yield more precise segmentations. The main idea is to supplement a usual contracting network by successive layers, where pooling operations are replaced by upsampling operators. Hence these layers increase the resolution of the output. A successive convolutional layer can then learn to assemble a precise output based on this information. The network consists of a contracting path and an expansive path, which gives it the u-shaped architecture. The contracting path is a typical convolutional network that consists of repeated application of convolutions, each followed by a rectified linear unit (ReLU) and a max pooling operation. During the contraction, the spatial information is reduced while feature information is increased. The expansive pathway combines the feature and spatial information through a sequence of up-convolutions and concatenations with high-resolution features from the contracting path. One important modification in the U-Net is that there are a large number of feature channels in the upsampling part, which allow the network to propagate context information to higher resolution layers. As a consequence, the expansive path is more or less symmetric to the contracting part and yields a u-shaped architecture. The network only uses the valid part of each convolution without any fully connected layers. To predict the pixels in the border region of the image, the missing context is extrapolated by mirroring the input image. This tiling strategy is important to apply the network to large images, since otherwise the resolution would be limited by the GPU memory.

In operation, the generator of the GAN, i.e., of the TG or BMD, is used without its discriminator. The GAN is (iteratively) applied to the continuously received sets of image data without the discriminator. The discriminator is only used for training of the GAN.

As described above the basic approach for training the GAN is to update its discriminator (i.e., the TDC or the MDC) with both, the predicted virtual topogram and the training (i.e., real) topograms, freeze the trainable parameters of the discriminator (TDC or MDC), and then update the trainable parameters of the generator (i.e., the trainable generator parameters or the trainable detector parameters) on how good the generator is at predicting virtual topograms which are classified as belonging to the training data by the discriminator (TDC or MDC). In particular, the trainable parameters in the generator may be updated while minimizing the binary cross entropy loss of the discriminator where output is supposed to be always 1. In one embodiment, the GAN is trained from an initial state based on estimates.

Instead of training the TG and BMD or IBMD with separate discriminators (TDC or MDC) only one joint discriminator may be used in training the TG and BMD or IBMD end-to-end.

For example, the BMD or IBMD for updating the representation of (internal) body landmarks may be a pre-trained landmark regressor (e.g., a GAN). While the TG is trained, the trainable parameters of the BMD or IBMD are not updated, and the training representations of (internal) body landmarks may be used for training the TG rather than the representations of (internal) body landmarks output by the BMD or IBMD. Alternatively, both networks, TG and BMD or IBMD, are trained end-to-end (i.e., the output of the BMD or IBMD is used in training TG).

For training the GAN (TG or BMD) various optimizers may be used, such as Adadelta, SGD, RMSprop, or Adam. The weights of the GAN are randomly initialized, but another initialization may be used. End-to-end training is performed, but one or more features may be set. Batch normalization, dropout, and data augmentation may be used. During the optimization, the different distinguishing features are learned. The features providing an indication of flow given input medical image of anatomy or tissue are learned.

The optimizer minimizes an error or loss, such as the Mean Squared Error (MSE), Huber loss, L1 loss, or L2 loss. The Huber loss may be less sensitive to outliers in data (represented in the training set by big variations in shape). Use of Huber loss helps capture better context. The patient's shape may be regressed better. In another embodiment, an L1 loss is used to better define lungs or other organs represented in the generated virtual topogram. Using the stacked U-Nets with L1 loss, the patient's shape and details for the lungs or other organs may be better than for Huber or L2 loss.

Further, the Wasserstein GAN architecture may be used, where, to stabilize the training, a Wasserstein loss with gradient penalty is applied. Other losses with or without a gradient penalty may also be used.

Using a GAN as the TG and additionally or alternatively as the BMD, in particular the IBMD, significantly increases the speed of generation and quality of the (live) virtual topograms.

According to a refinement, the image acquiring device is a stereo camera or includes a LIDAR sensor or an IR-sensor.

The depth information (sets of surface data) may be continuously acquired by the (2.5D) image acquiring device by triangulation in the images of the stereo camera.

Alternatively, the depth information (sets of surface data) may be continuously acquired by the (2.5D) image acquiring device including the depth sensor by means of LIDAR or time of flight of IR-pulses of the IR-sensor.

According to a refinement of the medical imaging system further includes as a medical imaging device one element or a combination of elements of the group including: an X-ray device; a computed tomography, CT, scanner; a magnet resonance imaging, MRI, scanner; a sonography device; a positron emission tomography, PET, scanner; a scintigraphy device; a single-photon emission computed tomography, SPECT, scanner; and an electrical impedance tomography, EIT, scanner. The medical imaging device is adjusted based on the continuously generated virtual topograms.

With reference to the generated (live) stream of virtual topogram, the medical imaging device (CT scanner, MRI scanner, etc.) is (autonomously) adjusted. For example, the subject may be positioned in the medical imaging device based on the generated (live) stream of virtual topogram such that the region of interest (ROI), for example head, heart, lungs, abdomen, extremities, etc., is better aligned inside the medical imaging device. Also, an imaging protocol of the medical imaging device (e.g., pulse sequence, timing of radiation, etc.) may be autonomously adjusted based on the generated (live) stream of virtual topograms.

The quality of medical imaging examinations is significantly increased (e.g., less motion artefacts, etc.) by adjusting the medical imaging device based on the generated topogram.

According to a refinement, the BMD and additionally or alternatively the TG is separately pre-trained before training of the MLA.

Using a pre-trained BMD or TG significantly reduces the time needed for training (fine-tuning) the MLA.

According to a refinement of the present invention the training topograms are acquired by one element or a combination of elements of the group including: X-ray imaging; computed tomography, CT, imaging; magnet resonance imaging, MRI; sonography; positron emission tomography, PET, imaging; scintigraphy; single-photon emission computed tomography, SPECT, imaging; and electrical impedance tomography, EIT, imaging.

Depending on which type of image is used as ground truth for training the MLA, the generated (live) virtual topograms resemble said type of image. For example, if topograms acquired by CT imaging (very high structural detail) are used as training topograms, the trained MLA generates (live) virtual topograms with the same features as the topograms acquired by CT imaging. If instead topograms acquired by MR imaging (detailed information about type of tissue) are used as training topograms, the trained MLA generates (live) virtual topograms with the same features as the topograms acquired by MR imaging.

Further, based on the (live) stream of virtual topograms generated by an MLA trained with topograms of a specific type medical imaging devices corresponding to the specific type can be adjusted. For example, an MRI device may be (autonomously) adjusted based on the (live) stream of virtual topograms of an MLA trained with topograms generated by MRI imaging.

Consequently, the MLA can be specifically trained to generate a (live) stream of virtual topograms having desired features that are useful for specific medical applications or medical questions.

BRIEF DESCRIPTION OF THE DRAWINGS

The present invention and its technical field are subsequently explained in further detail by (an) exemplary embodiment(s) shown in the drawing(s). The exemplary embodiment(s) only conduce(s) better understanding of the present invention and in no case is/are to be construed as limiting for the scope of the present invention. Particularly, it is possible to extract aspects of the subject-matter described in the figure(s) and to combine it with other components and findings of the present description or figure(s), if not explicitly described differently. Equal reference signs refer to the same objects, such that explanations from other figures may be supplementally used.

DETAILED DESCRIPTION

Figure 1:
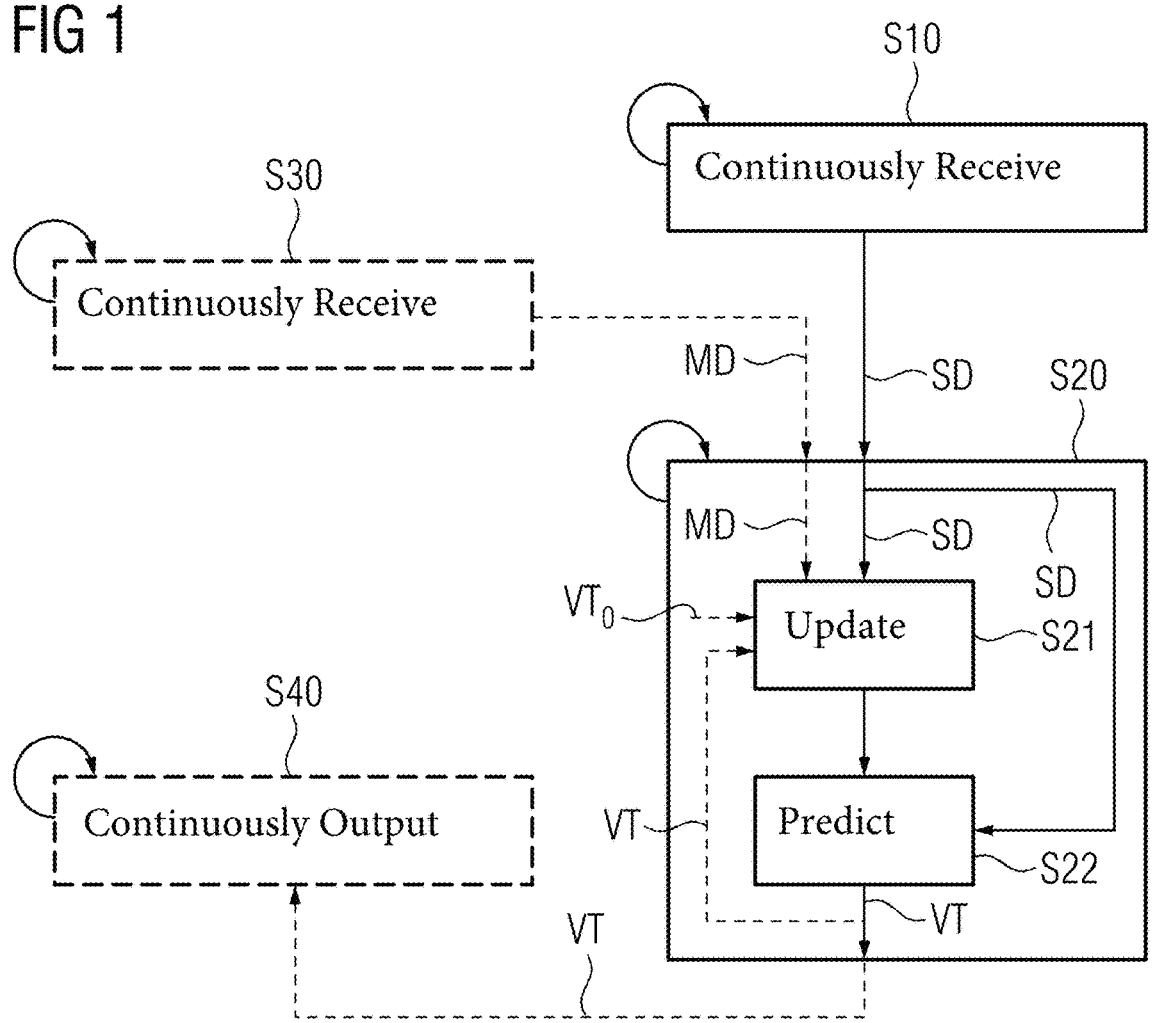
FIG. 1 shows a schematic flow-chart of an embodiment of the computer-implemented method of predicting a stream of virtual topograms according to the first aspect.

In FIG. 1, an embodiment of the computer-implemented method of predicting a stream of virtual topograms, in particular live virtual topograms, according to the first aspect as well as of the computer program according to the fourth aspect is schematically depicted. The embodiment of the computer-implemented method of predicting a stream of virtual topograms includes the acts continuously receiving S10 sets of image data, continuously generating S20, optionally continuously receiving S30 movement data, and optionally continuously outputting S40. The act of continuously generating S20 includes the acts of updating S21 and predicting S22.

In the act of continuously receiving S10 sets of image data, sets of image data including corresponding sets of surface data SD are continuously received. The image data and surface data are acquired by an image acquiring device (2, see FIGS. 2 and 5) including an image sensor and a depth sensor and includes information about the outer surface (skin or clothing) of a subject (6, see FIG. 2 5) including a 2 dimensional (2D) image of the subject and depth data for each pixel of the 2D image. The depth data includes a distance from the depth sensor to points on the outer surface of the subject corresponding to the respective pixel. The sets of image data including the corresponding sets of surface data SD may be received with a predefined clock rate or sample rate.

In the optional act of continuously receiving S30 movement data, movement data MD of the subject is continuously received. The movement data MD is acquired by the depth sensor or a separate movement sensor (4, 5, see FIGS. 2 and 5) and may include body movement data (movement of head, limbs, etc.), respiratory movement data (movement of the chest due to breathing), and additionally or alternatively heartbeat movement data (movement of the beating heart). The movement data MD may be received with a predefined clock or sample rate, in particular, the same clock or sample rate as the sets of image data including the corresponding sets of surface data SD.

In the act of continuously generating S20, the (live) virtual topograms VT are continuously generated based on each received set of image data including the corresponding set of surface data SD and optionally the received movement data MD. Thereto, a trained machine learning algorithm MLA receives each set of image data including the corresponding set of surface data SD and optionally the movement data MD as input and generates the (live) virtual topogram VT as output. Each (live) virtual topogram VT is a parametrized image and predicts the (current or live) internal anatomy of the subject or patient. The (live) virtual topogram VT may be generated with a predefined clock or sample rate, in particular, the same clock or sample rate as the sets of image data including the corresponding sets of surface data SD. Consequently, the (live) stream of virtual topograms of the subject or patient is generated based on the continuously received sets of image data including the corresponding sets of surface data SD and optionally the continuously received movement data MD.

In the act of continuously generating S20, the acts of updating S21 and predicting S22 may be iteratively executed until a predefined prediction stop criterion, in particular convergence of the predicted (live) virtual topograms VT, is reached.

In the (iterative) act of updating S21, a representation of body landmarks, in particular, a spatial marker map MM, is (iteratively) updated based on the current received set of image data including the corresponding set of surface data SD and optionally based on the current received movement data MD and further, in case the act is iteratively executed, based on the predicted (live) virtual topogram VT or, in the first iteration, a preliminary predicted virtual topogram $VT_0$. The preliminary predicted virtual topogram $VT_0$ may be predicted by a separate trained primary topogram generator $TG_p$ (not depicted) or may be the (live) virtual topogram VT predicted from the previous received set of surface data SD (and optionally the previous received movement data MD) in the previous sampling cycle. Further, the preliminary predicted virtual topogram $VT_0$ may be derived from a pre-stored phantom or a pre-stored topogram based on patient prior parameters (height, weight, BMI, age, sex) of the subject or patient.

Thereto, a trained body marker detector (BMD), in particular an internal body marker detector IBMD, of the MLA receives the current received set of image data including the corresponding set of surface data SD and optionally the current received movement data MD and further, in case the act is iteratively executed, the predicted (live) virtual topogram VT or, in the first iteration, the preliminary predicted virtual topogram $VT_0$ as input and (iteratively) updates the spatial marker map MM as output. The spatial marker map MM includes at least two locations of body landmarks (markers), in particular of internal body landmarks, that resemble characteristic anatomic features like lung top, liver top, kidney centre, etc.

In the (iterative) act of predicting S22, the (live) virtual topogram VT is (iteratively) predicted based on the current received set of image data including the corresponding set of surface data SD and based on the (current) updated spatial marker map MM. Thereto, a trained topogram generator TG of the MLA receives the current received set of image data including the corresponding set of surface data SD and the (current) spatial marker map updated by the IBMD as input and (iteratively) predicts the (live) virtual topogram VT as output.

In the optional act of continuously outputting S40, the generated (live) stream of virtual topograms VT is continuously output. In particular, each continuously generated (live) virtual topogram VT may be forwarded to an output device (3, see FIG. 5) i.e., a display device or an interface to a medical imaging device. Each (live) virtual topogram may be displayed as (live) stream on the display device or the medical imaging device may be (autonomously) adjusted based on the continuously generated (live) virtual topograms VT.

Figure 2:
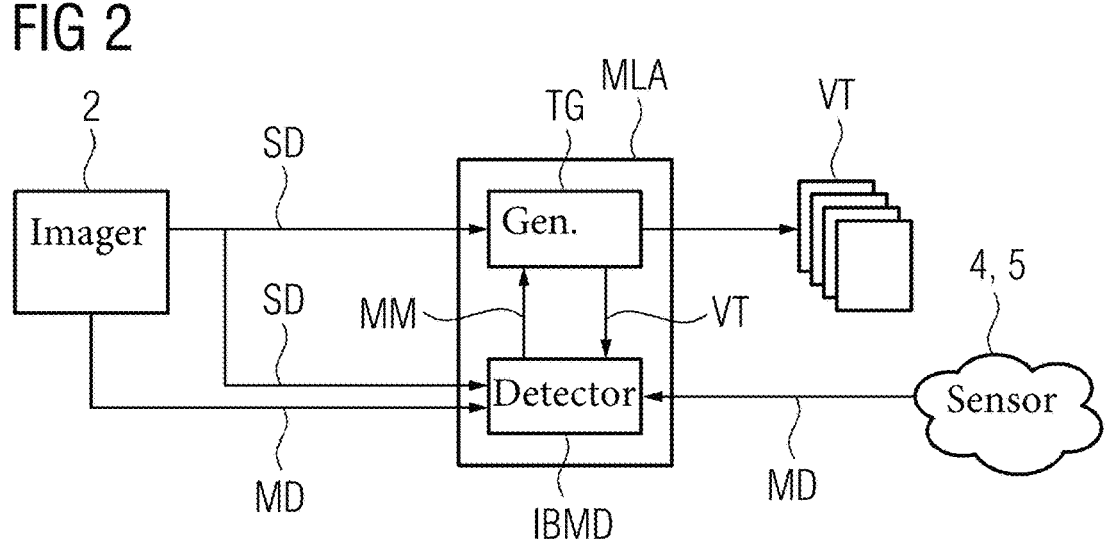
FIG. 2 shows a schematic view of an embodiment of the machine learning algorithm (MLA) trained for generating a stream of virtual topograms.

In FIG. 2, an embodiment of the MLA trained for generating (live) virtual topograms is schematically depicted. The MLA includes the IBMD and the TG and continuously receives the sets of image data including the corresponding sets of surface data SD from the image acquiring device 2 and optionally the movement data MD from image acquiring device 2 and additionally or alternatively from the movement sensor 4, 5.

The image acquiring device 2 is a 2.5D image acquiring device including an image sensor and a depth sensor that continuously acquire (with a predefined clock or sample rate) a 2D image of the patient (6, see FIG. 5) and depth data, i.e., distances from a front of the image acquiring device 2 or rather depth sensor to points on the outer surface of the subject or patient, for each pixel of the 2D image as one set of image data including corresponding surface data SD. The image acquiring device 2 may additionally derive the optional movement data MD from the continuously acquired sets of surface data SD.

The optional movement sensor continuously acquires (with a predefined clock or sample rate) the optional movement data MD and may be a respiratory sensor 4 (e.g., chest strap with strain gauge(s)) that continuously acquires respiratory movement data (movement of the chest due to breathing) and additionally or alternatively a heart sensor 5 (e.g., an ECG device, a pulse monitor, a blood pressure monitor, etc.) that continuously acquires heartbeat movement data.

Figure 7:
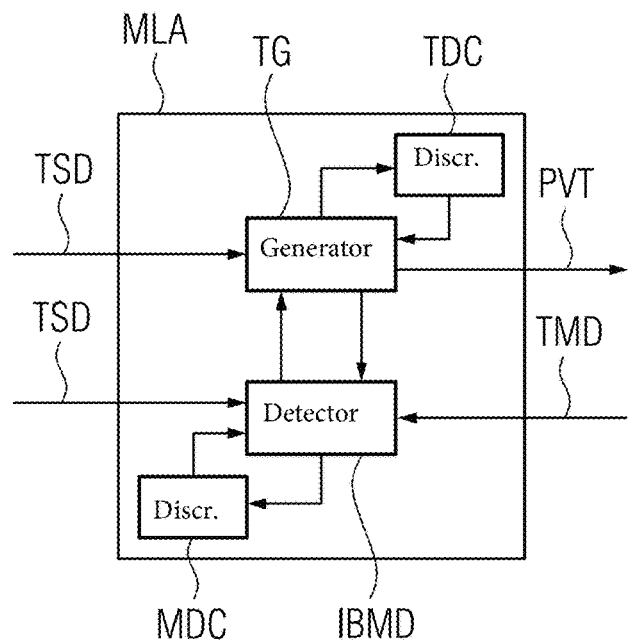
FIG. 7 shows a schematic view of the embodiment of the machine learning algorithm (MLA) in training for generating virtual topograms.

The IBMD and the TG are here exemplarily generative adversarial networks (GANs) each with a generator having a U-net architecture and with a discriminator (MDC, TDC, see FIG. 7). The IBMD has been trained to update the spatial marker map MM based on a set of image data including a corresponding set of surface data SD and optionally based on movement data MD and further optional, for iterative execution, based on a topogram (predicted by the TG). The TG has been trained to predict the (live) virtual topogram VT based on a set of image data including a corresponding set of surface data SD (the same as used by the IBMD) and based on a spatial marker map MM (updated by the IBMD).

The MLA continuously generates the (live) virtual topograms VT based on each received set of image data including the corresponding set of surface data SD and optionally further based on the received movement data MD. Thereby, the IBMD uses each received set of image data including the corresponding set of surface data SD and optionally the received movement data MD to update the spatial marker map MM and the TG uses the same received set of image data including surface data and the updated spatial marker map MM to predict the (live) virtual topogram VT.

Further, the IBMD and TG may be iteratively used to further improve the generated (live) virtual topograms VT. Thereto, the IBMD receives the (live) virtual topogram VT predicted by the TG as further input to update the spatial marker map MM. The spatial marker map MM and the (live) virtual topogram VT are in turn refined until the predicted (live) virtual VT topogram converges.

Each generated (live) virtual topogram VT is output to the output device for display or adjustment of the medical imaging device.

Figure 3:
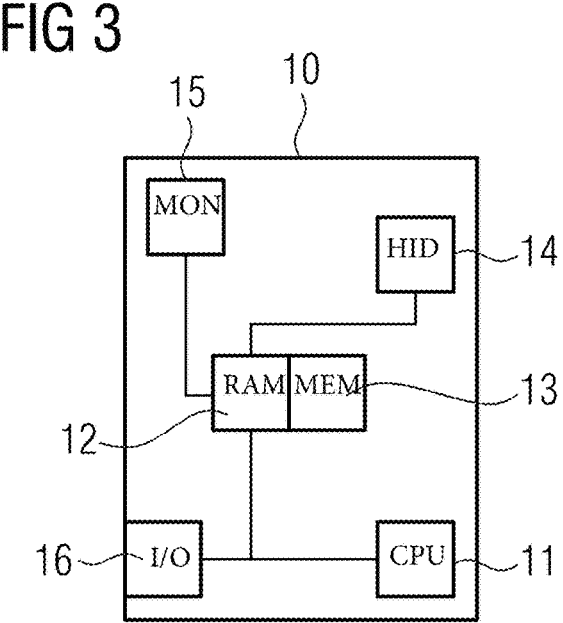
FIG. 3 shows a schematic view of an embodiment of the data processing system according to the second aspect.

In FIG. 3 an embodiment of the data processing system 10 according to the second aspect is schematically depicted.

The data processing system 10 may be a personal computer (PC), a laptop, a tablet, a server, a distributed system (e.g., cloud system) and the like. The data processing system 10 includes a central processing unit (CPU) 11, a memory having a random-access memory (RAM) 12 and a non-volatile memory (MEM, e.g., hard disk) 13, a human interface device (HID, e.g., keyboard, mouse, touchscreen etc.) 14, an output device (MON, e.g., monitor, printer, speaker, etc.) 15 and an interface (I/O) 16 for receiving and sending data. The CPU 11, RAM 12, HID 14 MON 15 and I/O 16 are communicatively connected via a data bus. The RAM 12 and MEM 13 are communicatively connected via another data bus.

The computer program according to the fourth aspect and schematically depicted in FIG. 1 can be loaded into the RAM 12 from the MEM 13 or another computer-readable medium 20. According to the computer program the CPU executes the acts of the computer-implemented method according to the first aspect and schematically depicted in FIG. 1. The execution can be initiated and controlled by a user via the HID 14. The status and/or result of the executed computer program may be indicated to the user by the MON 15 or output via the I/O 16. The result of the executed computer program may be permanently stored on the non-volatile MEM 13 or another computer-readable medium.

In particular, the CPU 11 and RAM 12 for executing the computer program may include several CPUs 11 and several RAMs 12 for example in a computation cluster or a cloud system. The HID 14 and MON 15 for controlling execution of the computer program may be included by a different data processing system like a terminal communicatively connected to the data processing system 10 (e.g., cloud system).

Figure 4:
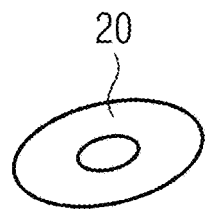
FIG. 4 shows a schematic view of an embodiment of the computer-readable medium according to the fifth aspect.

In FIG. 4, an embodiment of the computer-readable medium 20 according to the fifth aspect is schematically depicted.

Here, exemplarily a computer-readable storage disc 20 like a Compact Disc (CD), Digital Video Disc (DVD), High-Definition DVD (HD DVD) or Blu-ray Disc (BD) has stored thereon the computer program according to the fourth aspect of the present invention and as schematically shown in FIG. 1. However, the computer-readable medium may also be a data storage like a magnetic storage/memory (e.g., magnetic-core memory, magnetic tape, magnetic card, magnet strip, magnet bubble storage, drum storage, hard disc drive, floppy disc or removable storage), an optical storage/memory (e.g., holographic memory, optical tape, Tesa tape, Laserdisc, Phasewriter (Phasewriter Dual, PD) or Ultra Density Optical (UDO)), a magneto-optical storage/memory (e.g., MiniDisc or Magnetic-Optical Disk (MO-Disk)), a volatile semiconductor/solid state memory (e.g., Random Access Memory (RAM), Dynamic RAM (DRAM) or Static RAM (SRAM)) or a non-volatile semiconductor/solid state memory (e.g., Read Only Memory (ROM), Programmable ROM (PROM), Erasable PROM (EPROM), Electrically EPROM (EEPROM), Flash-EEPROM (e.g., USB-Stick), Ferroelectric RAM (FRAM), Magnetoresistive RAM (MRAM) or Phase-change RAM).

Figure 5:
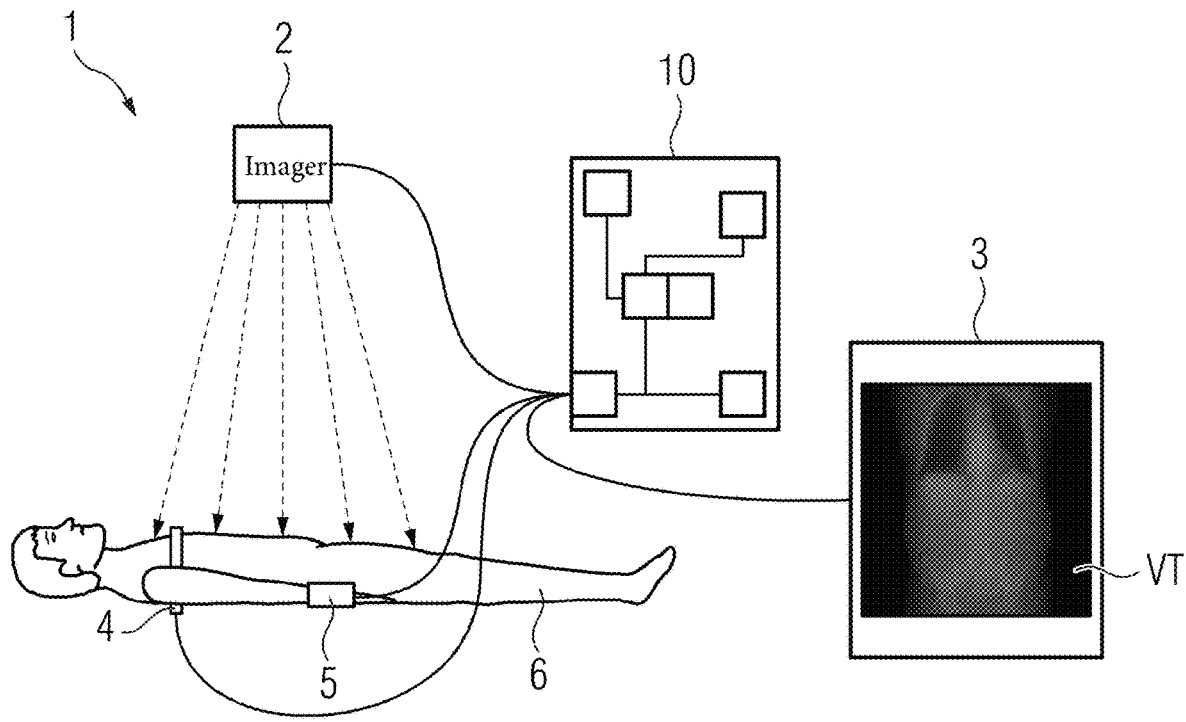
FIG. 5 shows a schematic view of an embodiment of the medical imaging system according to the third aspect.

In FIG. 5, an embodiment of the medical imaging system 1 according to the third aspect is schematically depicted. The medical imaging system 1 includes the (2.5D) image acquiring device 2, the output device 3, optionally the respiratory sensor 4 as movement sensor, optionally the heart sensor 5 as movement sensor, and the data imaging system 10 of FIG. 3.

The image acquiring device 2 is a 2.5D image acquiring device like a stereo camera including two image sensors or a 2.5D image acquiring device including an image sensor and a depth sensor like a LIDAR sensor or an IR-sensor (e.g., Microsoft Kinect 2, ASUS Xtion Pro). The image sensor continuously acquires the 2D image and the depth sensor continuously acquires corresponding depth data (distances to the outer surface of the subject 6) of each set of image data including the corresponding set of surface data SD with a predefined sample rate. The sets of image data including the corresponding sets of surface data SD are continuously (with the sample rate) forwarded to the data processing system 10 which is communicatively connected with the image acquiring device 2, for example via the I/O 16 of the data processing system 10. Further, the image acquiring device 2 may continuously (with the sample rate) derive the movement data MD from the continuously acquired sets of surface data SD and continuously forward the movement data MD together with the sets of image data including the corresponding sets of surface data SD to the data processing system 10. Further, the sets of surface data SD including the depth information could be reconstructed from multiple 2D images (i.e., the sets of image data) captured with just one single image sensor from multiple viewpoints or even from a single 2D image of the single image sensor using machine learning without any further image sensor or dedicated depth sensor.

The output device 3 may be a display device like a monitor, in particular the MON 15 of the data processing system 10, on which the continuously generated (live) virtual topograms VT are continuously displayed to a user (e.g., practitioner, radiologist, etc.). The output device 3 may also be an interface, in particular the I/O 16 of the data processing system, that can be connected to a medical imaging device (e.g., CT scanner, MRI device, X-ray device, etc.) which may be (autonomously) adjusted based on the continuously generated (live) virtual topograms VT.

The optional respiratory sensor 4 (movement sensor) is here exemplarily a chest strap with at least one integrated strain gauge. The movement of the chest of the subject 6 is (optionally) continuously detected with a predefined sample rate, optionally the same or a different sample rate as the image acquiring device 2, by the respiratory sensor 4 and the corresponding respiratory movement data is continuously (with the sample rate) forwarded as the movement data MD to the data processing system 10 which is communicatively connected with the respiratory sensor 4, for example via the I/O 16 of the data processing system 10.

The optional heart sensor 5 (movement sensor) is here exemplarily a pulse monitor worn on the wrist of the subject 6. The movement of the heart of the subject 6 is (optionally) continuously detected with a predefined sample rate, optionally the same or a different sample rate as the image acquiring device 2, by the heart sensor 5 and the corresponding heartbeat movement data is continuously (with the sample rate) forwarded as the movement data MD to the data processing system 10 which is communicatively connected with the heart sensor 5, for example via the I/O 16 of the data processing system 10.

The data processing system 10 continuously receives the (at least) the sets of image data including the corresponding sets of surface data SD from the image acquiring device 2 and optionally the movement data MD from at least one element of the group of elements including: the image acquiring device 2, the respiratory sensor 4 and the heart sensor 5. From each of the received sets of image data including the corresponding set of surface data SD and optionally further from the received movement data MD the data processing system 10 continuously generates the (live) virtual topograms VT with a predefined sample rate, optionally the same or a different sample rate as the image acquiring device 2. The (live) virtual topograms VT are thereby generated from each set of image data including the corresponding set of surface data SD and optionally from the corresponding movement data MD according to the computer-implemented method of FIG. 1. The continuously generated (live) virtual topograms VT are continuously forwarded to the output device 3 (e.g., the MON 15 of the data processing system).

Figure 6:
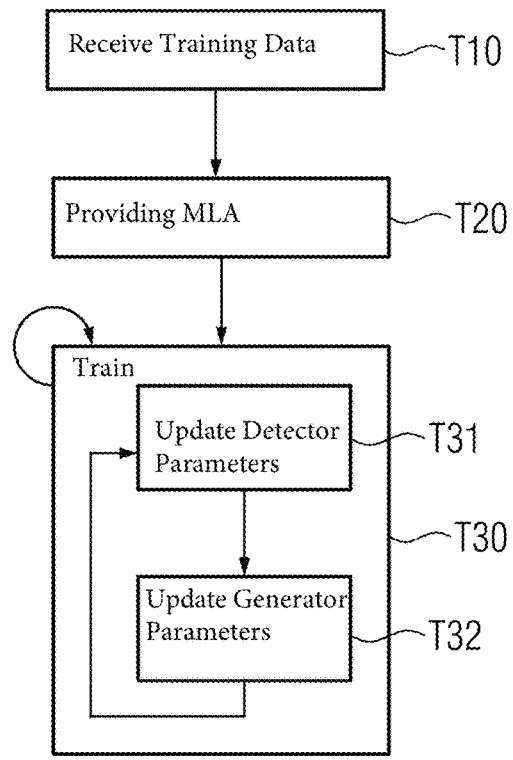
FIG. 6 shows a schematic flow-chart of an embodiment of the computer-implemented method of training MLAs for predicting virtual topograms according to the sixth aspect.

In FIG. 6, an embodiment of the computer-implemented method of training MLAs for predicting virtual topograms according to the sixth aspect and of the computer program according to the eighth aspect is schematically depicted. The embodiment of the computer-implemented method of training MLAs for predicting virtual topograms includes the acts receiving T10, providing T20, and training T30. The act of training T30 includes the acts updating T31 the trainable detector parameters and updating T32 the trainable generator parameters.

In the act of receiving T10, a set of training data is received. The set of training data includes training sets of image data including corresponding sets of surface data, corresponding training spatial marker maps and corresponding training topograms. Further, the set of training data may include corresponding training movement data like training respiratory movement data or training heartbeat movement data.

In the act of providing T20, an MLA (to be trained) is provided. The provided MLA is configured to continuously receive sets of image data including the corresponding sets of surface data with a predefined sample rate as input and to continuously generate with the same or a different sample rate virtual topograms from the continuously input sets of image data including the corresponding sets of surface data.

The provided MLA includes a body marker detector (BMD), in particular an internal body marker detector IBMD, (to be trained) and a TG (to be trained). The IBMD includes trainable detector parameters. The IBMD is configured to receive a set of image data including a corresponding set of surface data and optionally a topogram as input and to update a representation of body landmarks (markers), in particular a spatial marker map of (internal) body landmarks, based on the trainable detector parameters as output. The TG includes trainable generator parameters. The TG is configured to receive a representation of body landmarks, in particular a spatial marker map, and a set of image data including a corresponding set of surface data as input and to predict the virtual topogram based on the trainable generator parameters as output.

Optionally, the IBMD is further configured to receive movement data as further input besides the set of image data including the corresponding set of surface data and the optional topogram.

The IBMD and TG are here, exemplarily, GANs. The two GANs may have a joint discriminator for training, or each GAN may include a separate discriminator for training. Here, exemplarily, the IBMD includes a map discriminator MDC having trainable parameters and the TG includes a topogram discriminator TDC having trainable parameters for training.

In the act of training T30, the MLA is trained. The IBMD and TG of the MLA may be trained separately or end-to-end or both. Here, exemplarily, the IBMD and TG are trained end-to-end (with separate discriminators). Further, exemplarily, the IBMD and TG are iteratively trained, where the IBMD receives the virtual topogram predicted by the TG as further input.

In the act of updating T31, the trainable detector parameters, the trainable detector parameters of the IBMD are updated.

The IBMD receives one of the training sets of image data including the corresponding set of surface data of the training data and a corresponding topogram as input in each iteration. Further, the IBMD may receive corresponding training movement data as further input in each iteration. In the first iteration, the corresponding topogram is a pre-defined standard topogram ST (e.g., pre-stored normalized topogram) or a preliminary predicted virtual topogram $VT_0$ (e.g., virtual topogram VT predicted by the TG from the previous input training set of image data including surface data). Here, the corresponding topogram is the training topogram corresponding to the input training set of image data including the corresponding set of surface data. Based on the input training set of image data including the corresponding set of surface data and the corresponding topogram (and optionally the training movement data) the IBMD generates a spatial marker map in each iteration of the training.

In each iteration of the training, the trainable detector parameters of the (generator of the) IBMD are updated based on the result of a comparison between the spatial marker map generated from the input training set of image data including the corresponding set of surface data and corresponding topogram (and optionally training movement data) by the (generator of the) IBMD and the corresponding training spatial marker map or rather the set of training spatial marker maps. The comparison is made by the MDC of the IBMD. The trainable parameters of the MDC are also updated based on the result of said comparison. Thereby, the trainable detector parameters of the (generator of the) IBMD are updated in case the MDC did not classify the generated spatial marker map as the corresponding training spatial marker map or rather as belonging to the set of training spatial marker maps (insufficient generation). At the same time, the trainable parameters of the MDC are not updated (correct classification). In case the MDC did classify the generated spatial marker map as the corresponding training spatial marker map or rather as belonging to the set of training spatial marker maps, the trainable detector parameters of the (generator of the) IBMD are not updated (sufficient generation). At the same time, the trainable parameters of the MDC are updated (wrong classification).

In the act of updating T32 the trainable generator parameters, the trainable detector parameters of the TG are updated.

The TG receives the same training set of image data including the corresponding set of surface data of the training data as the IBMD and the spatial marker map generated by the IBMD as input in each iteration. Based on the input training set of image data including the corresponding set of surface data and the generated spatial marker map the TG generates a virtual topogram in each iteration of the training.

In each iteration of the training, the trainable detector parameters of the (generator of the) TG are updated based on the result of a comparison between the virtual topogram generated from the input training set of image data including the corresponding set of surface data and the generated spatial marker map by the (generator of the) TG and the corresponding training topogram or rather the set of training topograms. The comparison is made by the TDC of the TG. The trainable parameters of the TDC are also updated based on the result of said comparison. Thereby, the trainable generator parameters of the (generator of the) TG are updated in case the TDC did not classify the generated virtual topogram as the corresponding training topogram or rather as belonging to the set of training topograms (insufficient generation). At the same time, the trainable parameters of the TDC are not updated (correct classification). In case, the TDC did classify the generated virtual topogram as the corresponding training topogram or rather as belonging to the set of training topograms, the trainable generator parameters of the (generator of the) TG are not updated (sufficient generation). At the same time, the trainable parameters of the TDC are updated (wrong classification).

In FIG. 7, the embodiment of the MLA of FIG. 2 in training for generating virtual topograms is schematically depicted. The MLA includes the IBMD and TG. Here the IBMD and TG are each a GAN.

For training the IBMD and TG each include a separate discriminator, the MDC for the IBMD and the TDC for the TG. Alternatively, the IBMD and TG may share a joint discriminator. Here the IBMD and TG are exemplarily trained end-to-end. Alternatively, the IBMD and TG may be trained separately or first separately and then end-to-end.

The IBMD is being trained via iteratively updating the trainable detector parameters and the trainable parameters of the MDC as described above to generate (iteratively) form a set of image data and a corresponding set of surface data and a corresponding topogram (generated by the TG) (and optionally movement data) a spatial marker map (representation of (internal) body landmarks).

The TG is being trained via iteratively updating the trainable generator parameters and the trainable parameters of the TDC as described above to generate (iteratively) form the same set of image data including the corresponding set of surface data and the generated spatial marker map a virtual topogram.

Figure 8:
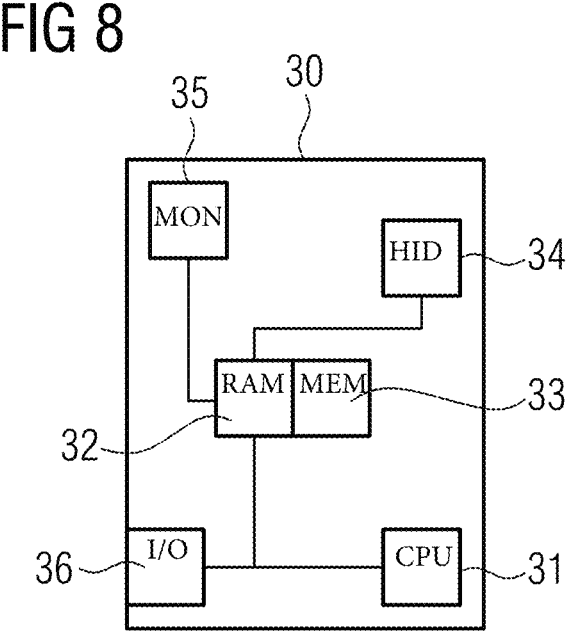
FIG. 8 shows a schematic view of an embodiment of the data processing system according to the seventh aspect.

In FIG. 8, an embodiment of the data processing system 30 according to the seventh aspect is schematically depicted.

The data processing system 30 may be a personal computer (PC), a laptop, a tablet, a server, a distributed system (e.g., cloud system) and the like. The data processing system 30 includes a central processing unit (CPU) 31, a memory having a random-access memory (RAM) 32 and a non-volatile memory (MEM, e.g., hard disk) 33, a human interface device (HID, e.g., keyboard, mouse, touchscreen etc.) 34, an output device (MON, e.g., monitor, printer, speaker, etc.) 35 and an interface (I/O) 36 for receiving and sending data. The CPU 31, RAM 32, HID 34 MON 35 and I/O 36 are communicatively connected via a data bus. The RAM 32 and MEM 33 are communicatively connected via another data bus.

The computer program according to the eighth aspect and schematically depicted in FIG. 6 can be loaded into the RAM 32 from the MEM 33 or another computer-readable medium 40. According to the computer program, the CPU executes the acts of the computer-implemented method according to the sixth aspect and schematically depicted in FIG. 6. The execution can be initiated and controlled by a user via the HID 34. The status and/or result of the executed computer program may be indicated to the user by the MON 35 or output via the I/O 36. The result of the executed computer program may be permanently stored on the non-volatile MEM 33 or another computer-readable medium.

In particular, the CPU 31 and RAM 32 for executing the computer program may include several CPUs 31 and several RAMs 32 for example in a computation cluster or a cloud system. The HID 34 and MON 35 for controlling execution of the computer program may be included by a different data processing system like a terminal communicatively connected to the data processing system 30 (e.g., cloud system).

Figure 9:
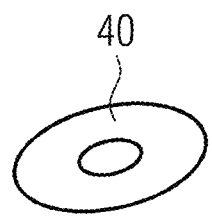
FIG. 9 shows a schematic view of an embodiment of the computer-readable medium according to the ninth aspect.

In FIG. 9, an embodiment of the computer-readable medium 40 according to the ninth aspect is schematically depicted.

Here, exemplarily a computer-readable storage disc 40 like a Compact Disc (CD), Digital Video Disc (DVD), High-Definition DVD (HD DVD) or Blu-ray Disc (BD) has stored thereon the computer program according to the eighth aspect of the present invention and as schematically shown in FIG. 6. However, the computer-readable medium may also be a data storage like a magnetic storage/memory (e.g., magnetic-core memory, magnetic tape, magnetic card, magnet strip, magnet bubble storage, drum storage, hard disc drive, floppy disc or removable storage), an optical storage/memory (e.g., holographic memory, optical tape, Tesa tape, Laserdisc, Phasewriter (Phasewriter Dual, PD) or Ultra Density Optical (UDO)), a magneto-optical storage/memory (e.g., MiniDisc or Magneto-Optical Disk (MO-Disk)), a volatile semiconductor/solid state memory (e.g., Random Access Memory (RAM), Dynamic RAM (DRAM) or Static RAM (SRAM)) or a non-volatile semiconductor/solid state memory (e.g., Read Only Memory (ROM), Programmable ROM (PROM), Erasable PROM (EPROM), Electrically EPROM (EEPROM), Flash-EEPROM (e.g., USB-Stick), Ferroelectric RAM (FRAM), Magnetoresistive RAM (MRAM) or Phase-change RAM).

Although specific embodiments have been illustrated and described herein, it will be appreciated by those of ordinary skill in the art that a variety of alternate and/or equivalent implementations exist. It should be appreciated that the exemplary embodiment or exemplary embodiments are only examples, and are not intended to limit the scope, applicability, or configuration in any way. Rather, the foregoing summary and detailed description will provide those skilled in the art with a convenient road map for implementing at least one exemplary embodiment, it being understood that various changes may be made in the function and arrangement of elements described in an exemplary embodiment without departing from the scope as set forth in the appended claims and their legal equivalents. Generally, this application is intended to cover any adaptations or variations of the specific embodiments discussed herein.

In the foregoing detailed description, various features are grouped together in one or more examples for the purpose of streamlining the disclosure. It is understood that the above description is intended to be illustrative, and not restrictive. It is intended to cover all alternatives, modifications and equivalents as may be included within the scope of the invention. Many other examples will be apparent to one skilled in the art upon reviewing the above specification.

Specific nomenclature used in the foregoing specification is used to provide a thorough understanding of the invention. However, it will be apparent to one skilled in the art in light of the specification provided herein that the specific details are not required in order to practice the invention. Thus, the foregoing descriptions of specific embodiments of the present invention are presented for purposes of illustration and description. They are not intended to be exhaustive or to limit the invention to the precise forms disclosed; obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. Throughout the specification, the terms "including" and "in which" are used as the plain-English equivalents of the respective terms "comprising" and "wherein," respectively. Moreover, the terms "first," "second," and "third," etc., are used merely as labels, and are not intended to impose numerical requirements on or to establish a certain ranking of importance of their objects. In the context of the present description and claims the conjunction "or" is to be understood as including ("and/or") and not exclusive ("either . . . or").

The invention claimed is:

1. A computer-implemented method of predicting a stream of virtual topograms, the method comprising:
   continuously receiving sets of image data of a subject; and
   continuously generating virtual topograms based on each received set of image data by a trained machine learning algorithm (MLA), the continuously generating comprising:
      updating a representation of body landmarks based on each received set of image data by a trained body marker detector (BMD) of the trained MLA; and
      predicting, by a trained topogram generator (TG) of the trained MLA, the virtual topogram based on input of the updated representation of body landmarks and on input of the corresponding set of image data to the TG of the trained MLA.

2. The method according to claim 1, wherein the sets of image data include corresponding sets of surface data (SD) of an outer surface of the subject, and
   wherein, in the act of updating, the representation of body landmarks is updated based on each received set of image data including the corresponding set of surface data by the trained BMD, and, in the act of predicting, the virtual topogram is predicted based on the updated representation of body landmarks and on the corresponding set of image data including the set of surface data by the trained TG.

3. The method according to claim 1, wherein the acts of updating and predicting are iteratively executed, and
   wherein, in the act of updating, the representation of body landmarks is updated based on each received set of image data and based on the predicted virtual topogram by the trained BMD.

4. The method according to claim 3, wherein, in a first iteration, the representation of body landmarks is updated based on each received set of image data and based on either a predefined standard topogram or a preliminary predicted virtual topogram by the trained BMD.

5. The method according to claim 4, wherein the preliminary predicted virtual topogram is either generated only based on the first received set of image data by either the trained TG or a trained primary or generated from a pre-stored phantom or a pre-stored topogram based on patient prior parameters.

6. The method according to claim 1, further comprising continuously receiving movement data of the subject, wherein the representation of body landmarks is updated further based on the received movement data by the trained BMD.

7. The method according to claim 1, wherein the trained TG and additionally or alternatively the trained BMD is a generative adversarial network.

8. The method according to claim 7 wherein the generative adversarial network comprises a Wasserstein generative adversarial network.

9. A medical imaging system for predicting a stream of virtual topograms), the medical imaging system comprising:
   an image sensor configured to acquire sets of image data of a subject;
   a computer communicatively connected to the image sensor, wherein the image sensor is configured to continuously forward the acquired sets of image data to the computer, the computer configured to continuously generate the virtual topograms based on each received set of image data by a trained machine learning algorithm (MLA), the virtual topograms continuously generated by update of a representation of body landmarks based on each received set of image data by a trained body marker detector (BMD) of the trained MLA and predict the virtual topogram based on input of the updated representation of body landmarks and on input of the corresponding set of image data to a trained topogram generator (TG) of the trained MLA; and
   an output device communicatively connected to the computer and configured to receive the continuously generated virtual topogram from the computer and to output the received virtual topogram.

10. The medical imaging system according to claim 9, wherein the image sensor further includes a depth sensor configured to acquire sets of surface data; and
   wherein the image sensor is configured to continuously forward the sets of image data including the corresponding acquired sets of surface data to the computer.

11. The medical imaging system according to claim 10, wherein the image sensor is a stereo camera or includes a LIDAR sensor or an IR-sensor.

12. The medical imaging system according to claim 9, further comprising a movement sensor communicatively connected to the computer and configured to acquire and continuously forward movement data of the subject to the computer.

13. The medical imaging system according to claim 9, further comprising a medical imaging device selected from the group of: an X-ray device; a computed tomography, scanner; a magnet resonance imaging scanner; a sonography device; a positron emission tomography scanner; a scintigraphy device; a single-photon emission computed tomography scanner; or an electrical impedance tomography scanner, wherein the medical imaging device is adjusted based on the continuously generated virtual topograms.

14. A method of training a machine learning algorithm, MLA, for predicting virtual topograms, the method comprising:

receiving a set of training data including training sets of image data, corresponding training representations of body landmarks, and corresponding training topograms;
providing the MLA configured to continuously receive sets of image data as input and to continuously generate virtual topograms from the continuously input sets of image data, the MLA comprising:
   a body marker detector (BMD) including trainable detector parameters and configured to receive the sets of image data as input and to update representations of body landmarks based on the trainable detector parameters as output; and
   a topogram generator (TG) including trainable generator parameters and configured to receive the representations of body landmarks and the sets of image data as input and to predict the virtual topograms based on the trainable generator parameters as output; and
training the MLA by:
   updating the trainable detector parameters based on a detector loss function penalising a difference between representations of body landmarks, which are generated from training sets of image data of the training data based on the trainable detector parameters, and the corresponding training representations of body landmarks of said training data; and
   updating the trainable generator parameters based on a generator loss function penalising a difference between virtual topograms, which are generated from training sets of image data of said training data and corresponding representations of body landmarks based on the trainable generator parameters, and the corresponding training topograms of said training data.

15. The method according to claim 14, wherein the training sets of image data include corresponding training sets of surface data, and
   wherein, in the act of updating the trainable detector parameters, the representations of the body landmarks are generated from the training sets of image data including the corresponding training sets of surface data, and, in the act of updating the trainable generator parameters, the virtual topograms are generated from the training sets of image data including the corresponding sets of surface data.

16. The method according to claim 14, wherein the BMD and additionally or alternatively the TG is separately pre-trained before training of the MLA.

17. The method according to claim 14, wherein the TG and additionally or alternatively the BMD is a generative adversarial network, and
   wherein updating the trainable generator parameters and detector parameters, respectively, includes comparing of the generated virtual topograms with the training topograms and the generated representations of body landmarks with the training representations of body landmarks, respectively, by a topogram discriminator and a map discriminator, respectively, and simultaneously updating trainable parameters of the TDC and of the MDC, respectively.

18. The method according to claim 14, wherein the training topograms are acquired by one element or a combination of elements of the group comprising: X-ray imaging; computed tomography imaging; magnet resonance imaging; sonography; positron emission tomography imaging; scintigraphy; single-photon emission computed tomography imaging; and electrical impedance tomography imaging.

19. The method according to claim 14, wherein the set of training data further includes training movement data, wherein the BMD is further configured to receive movement data as further input, and wherein, in the act of updating the detector parameters, the representations of body landmarks are generated further from the training movement data.

* * * * *